United States Patent [19]
Stoltz

[11] 4,225,994
[45] Oct. 7, 1980

[54] POWER-OPERATED TOOTHBRUSH

[75] Inventor: Werner Stoltz, Friedrichsdorf, Fed. Rep. of Germany

[73] Assignee: Blendax-Werke - R. Schneider GmbH & Co., Mainz, Fed. Rep. of Germany

[21] Appl. No.: 970,227

[22] Filed: Dec. 18, 1978

Related U.S. Application Data

[63] Continuation-in-part of Ser. No. 857,030, Dec. 2, 1977, Pat. No. 4,149,291.

[30] Foreign Application Priority Data

Dec. 23, 1977 [DE] Fed. Rep. of Germany ....... 2757590

[51] Int. Cl.$^3$ ............................................. A46B 13/02
[52] U.S. Cl. .................................... 15/22 R; 200/330
[58] Field of Search .................. 15/22 R, 22 A, 22 C, 15/23, 24, 28, 29; 200/330, 340; 310/50, 68 B, 68 A, 68 E

[56] References Cited

U.S. PATENT DOCUMENTS

| 3,829,922 | 8/1974 | Koblanski | 15/23 |
| 3,945,076 | 3/1976 | Sung | 15/22 R |

Primary Examiner—Edward L. Roberts
Attorney, Agent, or Firm—Connolly and Hutz

[57] ABSTRACT

A mechanically or electrically operated toothbrush is actuated by a reversing switch operated by a movable handle section mounted over the housing of the toothbrush. The direction of the rotation of the toothbrush is changed by movement of the handle relative to the housing while the brush is applied to the teeth to provide the desired direction for the section of teeth being brushed.

8 Claims, 6 Drawing Figures

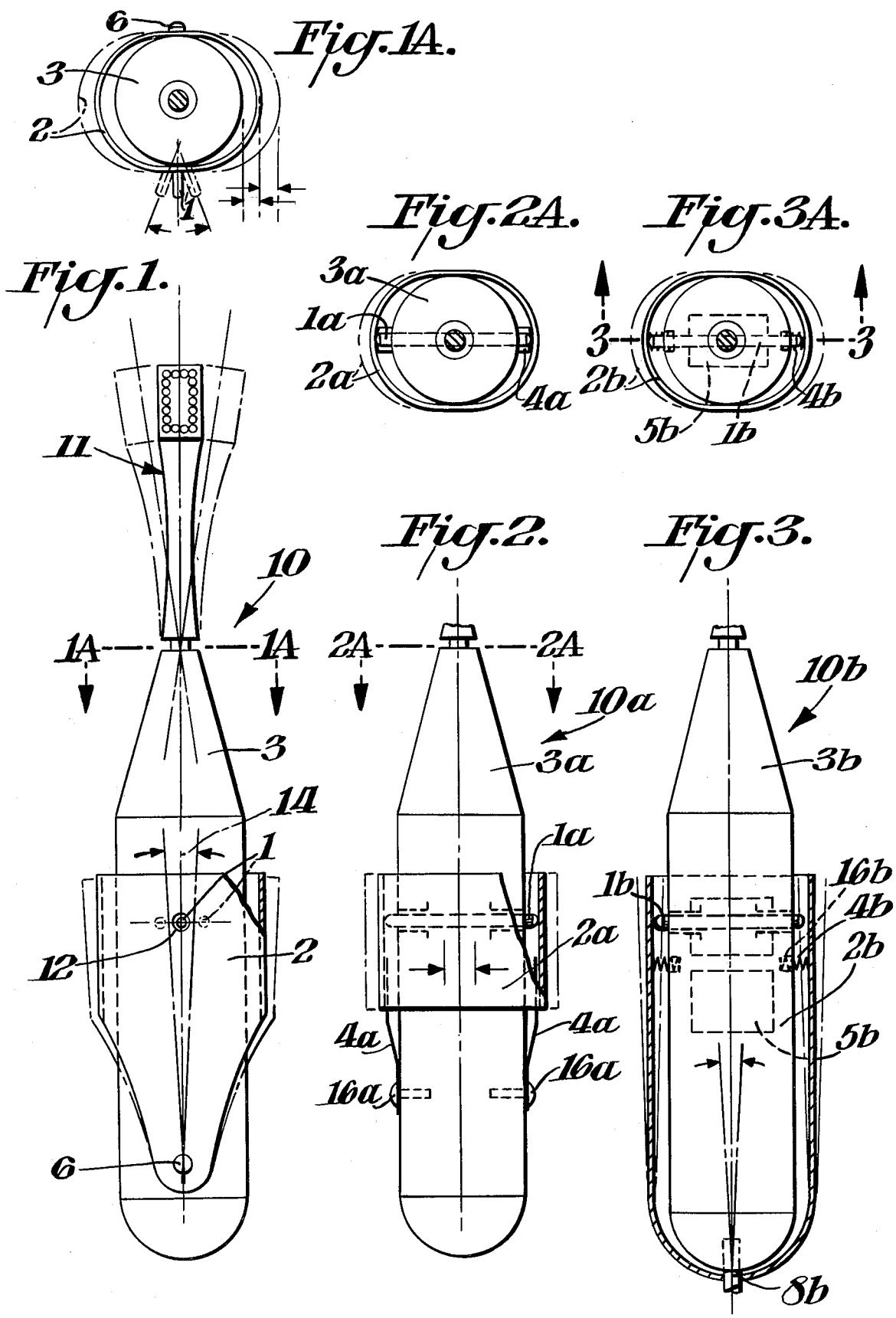

POWER-OPERATED TOOTHBRUSH

CROSS REFERENCE TO RELATED APPLICATIONS

This application is a continuation-in-part of application for U.S. Pat. Ser. No. 857,030, filed Dec. 2, 1977, now U.S. Pat. No. 4,149,291 by the same inventor.

BACKGROUND OF THE INVENTION

The subject matter of the earlier patent application Ser. No. 857,030, filed Dec. 2, 1977 is a mechanically or electrically operated toothbrush, incorporated in a housing, which is characterized in that situated at the rotation output end is an eccentrically mounted disk, wherein one or more funnel-shaped openings are eccentrically situated, serving as the end bearing for receiving a drive shaft whose outer support with ball head or of flexible material is situated in the toothbrush housing and whose end is formed directly as a holder for a push-in brush. By the arrangement of the drive of this toothbrush, it is possible to carry out a rotary to elliptical cleaning movement desired in dental medicine.

In this connection, however, there arises the necessity to vary the rotational direction of the cleaning movement, depending on the application of the brush to the dentition. This occurs according to a preferred design of the earlier patent application by the arrangement of a reversing switch by means of which the rotational direction of the rotating output disk may be varied.

Although such reversing switch per se provides for a satisfactory handling of the switching of the toothbrush according to the earlier patent, this solution may seem cumbersome to some users to the extent that they must undertake a switching after the cleaning of every tooth section on the inside and outside of the dentition. For the non-mechanically inclined user or for children, problems could result therefrom.

This also holds true with respect to a further preferred embodiment of the earlier patent application, according to which the reversing switch is formed in such a manner that it may be actuated by lip or pressure. This too, requires a certain dexterity of the user. Furthermore, the formation of such a switch is visually troublesome and upon utilization also annoying to the user.

Furthermore, known from DT-OS No. 2 363 364 is an electric toothbrush whose operation is initiated by the pressure of the toothbrush on the teeth. Entirely aside from the fact that this does not cause a "reversal" of the rotational direction of the brush, the actuation is not afforded by the variable pressure forces exerted by the user.

SUMMARY

According to the current invention, a power-operated toothbrush is provided which exerts an elliptical to a rotary rotational movement and is in a position to change the particular rotational movement by means of an automatic switching device during its utilization.

This problem is solved in that in the toothbrush housing there is provided a toggle or slider switch for the reversal of the rotational direction which may be actuated by means of a handle held by the user in the actuation of the electric toothbrush. This handle, as opposed to the housing part of the driven toothbrush, is movably mounted in such a manner that relative thereto it is tiltable, slidable or pivotable. The handle is connected with the actuating member of the reversing switch in such a manner that such switch is actuated in the appropriate rotational direction, as the case may be, if the position of the brush is changed relative to the handle part by pressure on the teeth.

The mounting of the handle section on the housing of the toothbrush may take place, for example, by means of leaf springs, slidable connecting rods, joints, etc.

BRIEF DESCRIPTION OF THE DRAWINGS

Novel features and advantages of the present invention will become apparent to one skilled in the art from a reading from the following description in in conjunction with the accompanying drawings wherein similar reference characters refer to similar parts and in which:

FIG. 1 is a side elevational view of a power-operated toothbrush and handle switch control;

FIG. 1A is a cross-sectional view taken through FIG. 1 along the line 1A—1A;

FIG. 2 is a side elevational view of a power housing and alternate handle switch control;

FIG. 2A is a cross sectional view taken through FIG. 2 along the line 2A—2A;

FIG. 3 is a cross-sectional view taken through FIG. 3A along line 3—3; and

FIG. 3A is a top plan view of a power housing and a further alternate handle switch control.

DESCRIPTION OF THE PREFERRED EMBODIMENTS

FIGS. 1 and 1A show a power toothbrush 10 having a movable yoke-shaped handle section 2 mounted upon housing 3. FIGS. 2 and 2A have a shorter sleeve-shaped movalbe handle section 2a mounted upon housing section 3a. FIGS. 3 and 3A have a casing shaped handle section 2b nearly completely enclosing housing 3b. The movement of handle section 2, 2a or 2b relative to housing 3, 3a or 3b when the brush is applied to the teeth, depending on the position of the applied brush, actuates reversing switch 1, 1a, or 1b. Reversing switch 1, 1a or 1b is constructed and arranged so that the direction of rotation of the power toothbrush 11 synchronizes with the particular positions at which the brush is applied to the teeth to provide desirable brushing action.

In FIG. 1 handle section 2 is movably mounted relative to housing 3 on pivots 6 near the bottom of housing 3. Handle 2 engages toggle switch lever 1 at slot 12 whose center line 14 has an angular movement relative to handle pivot 6 of approximately 6°. FIG. 2 shows how the 6° angular movement of handle 2 is converted into a lateral 40° movement of toggle switch lever 1 to actuate the switch to provide reversing movement in two different directions. FIGS. 2 and 2A show handle sleeve 2a mounted on leaf springs 4a whose lower ends are secured to housing 3 by mounting screws 16a. Lateral movement of handle sleeve 2a from the neutral solid line position to the phantom outline positions shows the full range of movement of switch 1a to accomplish reversing movement in two different directions. Switch 1a is turned off in the central solid line position. It is also possible, however, to provide a separate switch for turning brush 10a on and off.

FIGS. 3 and 3A show a casing-shaped movable handle section 2b which pivots about flexible mounting element 8b mounted at the bottom of housing 2b. Handle 2b may accordingly rock 6° relative to housing 3b to actuate switch 1b in a manner similar to switch 1a in FIG. 2. FIG. 3 also shows a further reversing switch 5b, actuated for example by gravity. The two different switches provide a different switching actuation for the uper and lower jaws to suit the different directions of power brushing respectively required. Handle casing 2b is biased in the neutral position by a pair of coil springs 4b inserted in sockets 16b in the sides of housing 3b acting in the direction of movement of switch 1b.

The transition from housing to handle is sealed preferably in a manner known per se, e.g. by bellows, not shown, in order to prevent the intrusion of water or tooth paste.

The operating mechanism of the novel power toothbrush is explained again in detail as follows:

Upon the application of pressure by the brush on the teeth, the reversing switch is actuated by the shifting of the position of the handle with respect to the housing section; the brush is set into a rotary or elliptical motion by means of the arrangement described in U.S. Patent Application Ser. No. 857,030, filed Dec. 2, 1977. With a change of the brush position by the application on another tooth section, the position of the handle section necessarily changes with respect to the housing, whereby the reversing switch is actuated respectively and the rotational direction is changes accordingly should it be required depending on the position of the brush. In this manner, the correct rotational direction of the brush, i.e. from the gums out, is always automatically afforded.

As for the rest of the opertion, that of the embodiments described in U.S. Patent Application Ser. No. 857,030, filed Dec. 2, 1977 also holds true for this novel toothbrush.

I claim:

1. A power operated toothbrush comprising a housing, a replaceable movable brush mounted on the end of the housing, power-operated means in the housing for causing the brush to move in a predetermined path of movement, a reversing switch on the housing for causing the power-operated means to move the brush in two different directions, a handle section, coupling means connecting the handle section to the reversing switch for actuating it, a handle section motion-permitting means mounting the handle section on the housing whereby movement of the handle section relative to the housing causes the actuation of the reversing switch in both of its directions.

2. A power operated toothbrush as set forth in claim 1, wherein the handle section comprises a yoke-shaped sleeve and pivot means connecting the yoke-shaped sleeve to the housing.

3. A power operated toothbrush as set forth in claim 2, wherein the reversing switch comprises a toggle switch and the coupling means comprises a hole within the yoke-shaped sleeve engaged by the toggle switch.

4. A power operated toothbrush as set forth in claim 1, wherein the handle section comprises an annular sleever, the reversing switch comprises a reciprocating switch extending laterally through the housing on two sides thereof for actuation by the inside of the sleeve in two directions and spring means reacting between the housing and the inside of the sleeve for maintaining it in a neutral position.

5. A power operated toothbrush as set forth in claim 4, wherein the spring means comprises leaf springs connected between the sleeve and the housing.

6. A power operated toothbrush as set forth in claim 1, wherein the handle section comprises a casing surrounding the space from the outside of the housing, the reversing switch comprising a laterally moving switch extending from both sides of the housing in contact with the inside of the casing and spring means reacts between the inside of the casing and the outside of the housing to maintain the casing in a neutral position relative to the housing.

7. A power operated toothbrush as set forth in claim 6, wherein the spring means comprises a pair of coil springs.

8. A power operated toothbrush as set forth in claim 1, wherein a gravity operated reversing switch is also provided in the housing whereby a second mode of switch operation is provided for the brushing.

* * * * *